(12) United States Patent
McIntyre et al.

(10) Patent No.: US 8,209,007 B2
(45) Date of Patent: Jun. 26, 2012

(54) SWITCHING CIRCUIT

(75) Inventors: Allister R. McIntyre, Newtownards (GB); John McCune Anderson, Holywood (GB); Johnny Houston Anderson, Holywood (GB)

(73) Assignee: Heartsine Technologies Ltd., Belfast (GB)

( * ) Notice: Subject to any disclaimer, the term of this patent is extended or adjusted under 35 U.S.C. 154(b) by 548 days.

(21) Appl. No.: 12/299,362

(22) PCT Filed: May 1, 2007

(86) PCT No.: PCT/EP2007/003834
§ 371 (c)(1),
(2), (4) Date: Nov. 3, 2008

(87) PCT Pub. No.: WO2007/131625
PCT Pub. Date: Nov. 22, 2007

(65) Prior Publication Data
US 2009/0187224 A1 Jul. 23, 2009

(30) Foreign Application Priority Data
May 12, 2006 (IE) .................................. S2006/0379

(51) Int. Cl.
*A61N 1/39* (2006.01)
(52) U.S. Cl. .......................................................... 607/5
(58) Field of Classification Search ........................ 607/5
See application file for complete search history.

(56) References Cited

U.S. PATENT DOCUMENTS

| 3,450,974 | A | 6/1969 | Berlin | |
|---|---|---|---|---|
| 4,426,603 | A | 1/1984 | Mustoe | |
| 5,239,203 | A | 8/1993 | Thorngren | |
| 6,980,856 | B2 * | 12/2005 | Sullivan et al. | 607/4 |
| 6,996,436 | B2 | 2/2006 | Allen et al. | |
| 2003/0023276 | A1 * | 1/2003 | Allen et al. | 607/5 |
| 2003/0088283 | A1 * | 5/2003 | Ostroff | 607/5 |

FOREIGN PATENT DOCUMENTS

GB  1 208 489 A  10/1970

OTHER PUBLICATIONS

International Search Report dated Sep. 20, 2007 (Four (4) pages.

* cited by examiner

*Primary Examiner* — Michael Kahelin
(74) *Attorney, Agent, or Firm* — Sullivan & Worcester LLP; Christopher T. McWhinney

(57) ABSTRACT

An H-bridge switching circuit for an automated external defibrillator comprises an SCR (D8) in one of the high legs of the circuit and a control means (D1-D7) associated with the SCR which is operative to switch the SCR on automatically in response to a voltage change across the SCR corresponding to the switching device in the diagonally opposite leg of the H-bridge turning on. The control means comprises a capacitor (D1) and the voltage on the capacitor changes when the diagonally opposite switching device turns on, the change in capacitor voltage lagging the change in voltage across the SCR and the SCR being turned on when the difference between the capacitor voltage and the voltage across the SCR exceeds a predetermined threshold.

4 Claims, 5 Drawing Sheets

SWITCHING CIRCUIT

CROSS REFERENCE TO RELATED APPLICATIONS

This application is a national stage of International Application No. PCT/EP2007/003834, filed May 1, 2007, which claims priority under 35 U.S.C. §119 to Ireland Patent Application No. S2006/0379 filed May 12, 2006, the entire disclosure of which is herein expressly incorporated by reference.

BACKGROUND AND SUMMARY OF THE INVENTION

This invention relates to a switching circuit, in particular for switching electrical bipolar power to a load in an automatic external defibrillator.

Automatic external defibrillators (AEDs) commonly deliver electrotherapy by the bipolar transfer of energy into a patient. Appropriate therapy demands a significantly high voltage, in excess of 1000 volts at a current in excess of 30 amps. This puts exceedingly stringent requirements on the design of the switching circuit used to deliver such therapy, not only on the components needed to deliver such energy with integrity and reliability, but also on the safety of such devices.

A known switching circuit is an H-bridge, so-called from its typical graphical representation in the form of an "H". An H-bridge can be used in many situations where it is desired to reverse the direction of current through a load, for example to drive a reversible DC electric motor or, in the case of an AED, to reverse the direction of current through a patient's torso. In general, an H-bridge has four solid state or mechanical switching devices arranged respectively in the four "legs" of the H which are switched on in alternate diagonal pairs to deliver a current to a load first in one direction and then the other from a voltage source.

An example of an H-bridge 10 used for current switching in an AED is shown in FIG. 1, where the load is the patient and the voltage, derived from a capacitor V, is applied via electrodes applied to the patient's chest. In the H-bridge 10 the switching devices S11 and S12 in the 'high' (i.e. non-grounded) legs of the H-bridge are silicon controlled rectifiers (SCRs) and the switching devices S13 and S14 in the 'low' legs of the H-bridge are insulated gate bipolar transistors (IGBTs). An SCR is triggered by a pulse of a minimum duration on its gate at a specified voltage above that of its cathode but it is susceptible to spontaneous switch-on if the rate of increase of voltage across it exceeds a specified limit. It is switched off by the reduction of the current through it below a specified level. An IGBT is switched on by, and for the duration of, a voltage applied to its gate greater than a specified level above its emitter voltage. It is switched off by the removal of this trigger voltage. The operation of the H-bridge 10 is as follows.

The first part of the bipolar delivery into the load is initiated by switching on the IGBT S13. This is achieved by applying and maintaining an external trigger signal Control 3 to its gate. The capacitor V is then charged (using an external charging circuit, not shown) from zero to the required voltage for delivery into the load at the required current. It is necessary that the capacitor V is not pre-charged prior to S13 being switched on since any voltage appearing instantaneously across an SCR, such as the SCR S11, may spontaneously trigger the SCR due to the rate of increase in voltage across it. When the required voltage on the capacitor V is reached, the diagonally opposite SCR S12 is switched on by applying a pulse Control 2 to its gate via a coupling transformer (not shown). When both switches S12 and S13 are conducting, current passes through the load in one direction. At a chosen time, the IGBT S13 is switched off by the removal of the trigger signal Control 3 on its gate. This removes the current through the SCR S12 causing it to switch off, thereby disconnecting the load from the voltage supply V.

The second part of the bipolar delivery into the load is initiated by switching on the IGBT S14 by applying and maintaining an external trigger signal Control 4 to its gate. Immediately afterwards, the diagonally opposite SCR S11 is switched on by a pulse Control 1 to its gate via a coupling transformer. Now that both switches S11 and S14 are conducting, current passes through the load in the opposite direction to that during the first part of the bipolar discharge. The cycle ends when either the IGBT S14 is switched off, thereby removing the current through the SCR S11 which consequently switches off, or by the discharge of the primary voltage source V to a point at which the SCR S11 cannot support the reduced current flow in the load.

A limitation of the known H-bridge is the complexity of the circuitry needed to drive the SCRs S11 and S12. In both cases, since the voltage on the cathodes of the SCRs can rise to the same potential as the voltage across the capacitor V, the gates must be decoupled with transformers. from external circuits to inject the pulses needed for switching them on. Further, considerable additional circuitry is required to implement hardware interlocking circuits to ensure the safety and integrity of the operation of the bridge.

U.S. Pat. No. 6,996,436 teaches the replacement of one of the SCRs by an uncontrolled solid-state device (USD) having Shockley device characteristics. This eliminates the necessity for one transformer coupling and, since the USD switches as a direct consequence of the action of the IGBTs, the hardware interlocking requirements for integrity are also reduced. However, a further limitation is imposed in that due to its Shockley characteristics the USD cannot switch below a certain threshold voltage. Therefore, when used in an automatic external defibrillator, it will not be possible to deliver energy below a level defined by the lowest voltage level at which the USD can operate.

It is an object of this invention to provide an external defibrillator having a switching circuit which avoids or mitigates these disadvantages.

Accordingly, the present invention provides an external defibrillator comprising an H-bridge for delivering bipolar electrotherapy to a patient, the H-bridge having a respective solid state switching device in each of its four legs, the switching device in at least one of the high legs of the H-bridge including an SCR, the H-bridge further comprising a control circuit which automatically generates a voltage spike to turn on the SCR in response to a voltage change across the SCR which occurs when the switching device in the diagonally opposite low leg turns on.

BRIEF DESCRIPTION OF THE DRAWINGS

An embodiment of the invention will now be described, by way of example, with reference to the accompanying drawings, in which.

DETAILED DESCRIPTION OF THE DRAWINGS

Figure 1:
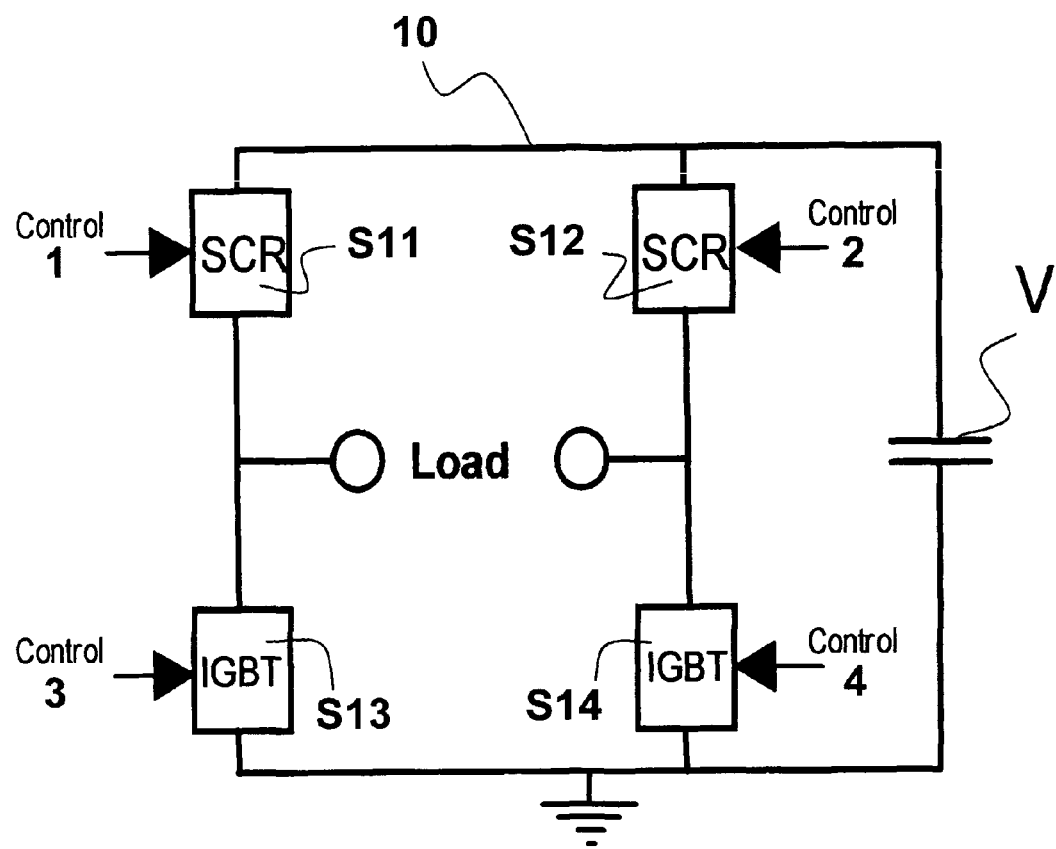
FIG. 1 (previously described) is a circuit diagram of an H-bridge 10 according to the prior art.

In the drawings, the same or equivalent components have been given the same reference numerals/letters.

Figure 2:
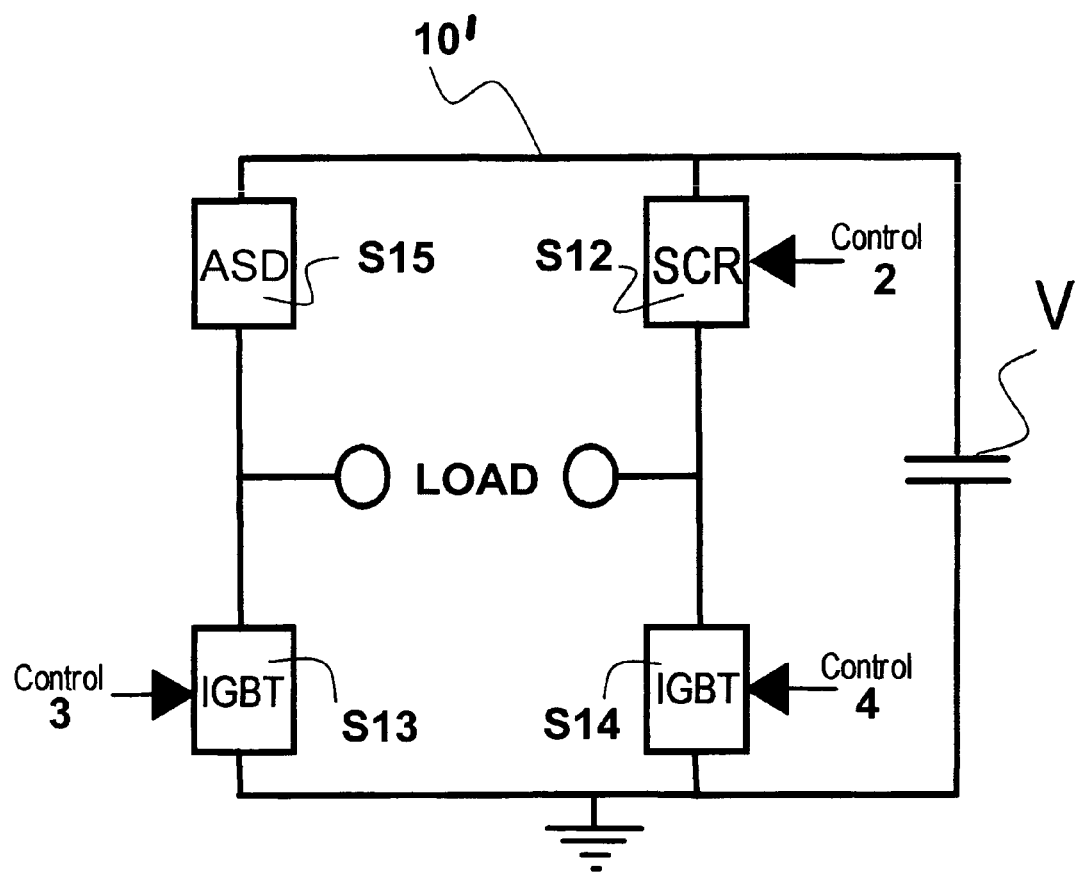
FIG. 2 is a circuit diagram of an H-bridge 10' according to the embodiment of the invention.
Figure 3:
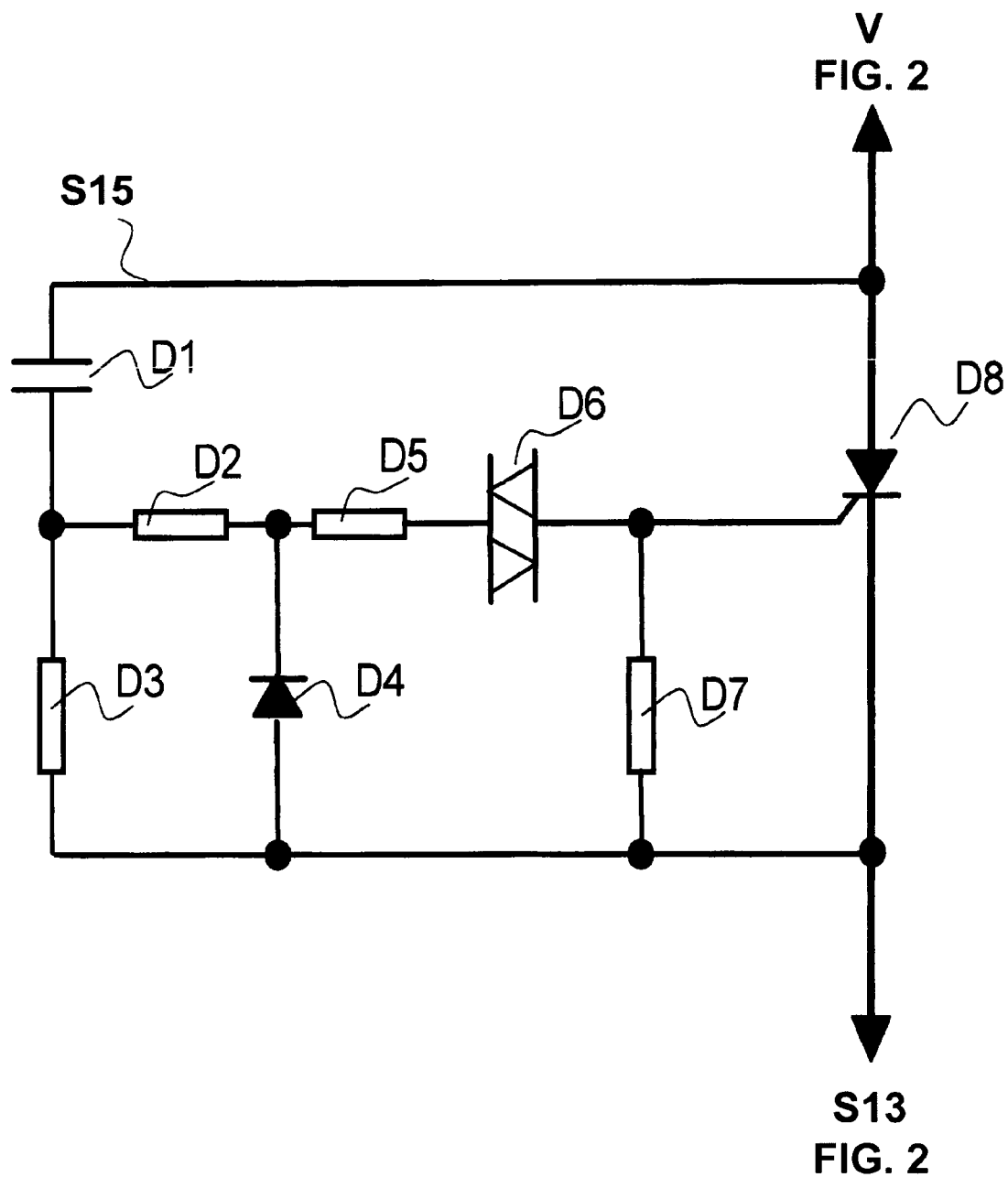
FIG. 3 is a circuit diagram of the automatic switching device in the H-bridge of FIG. 2.
Figure 4:
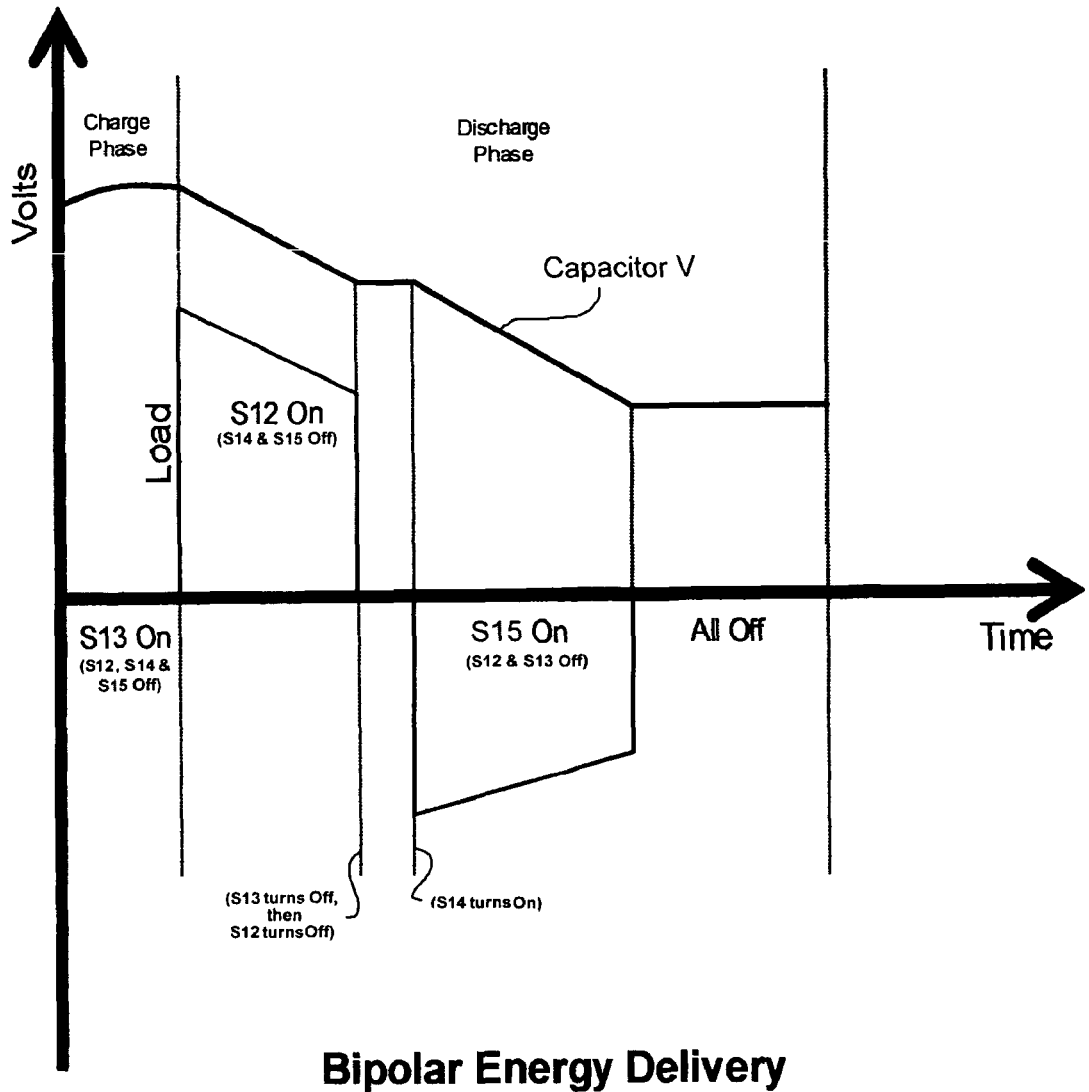
FIG. 4 is a waveform diagram illustrating the external operation of the H-bridge of FIG. 2.
Figure 5:
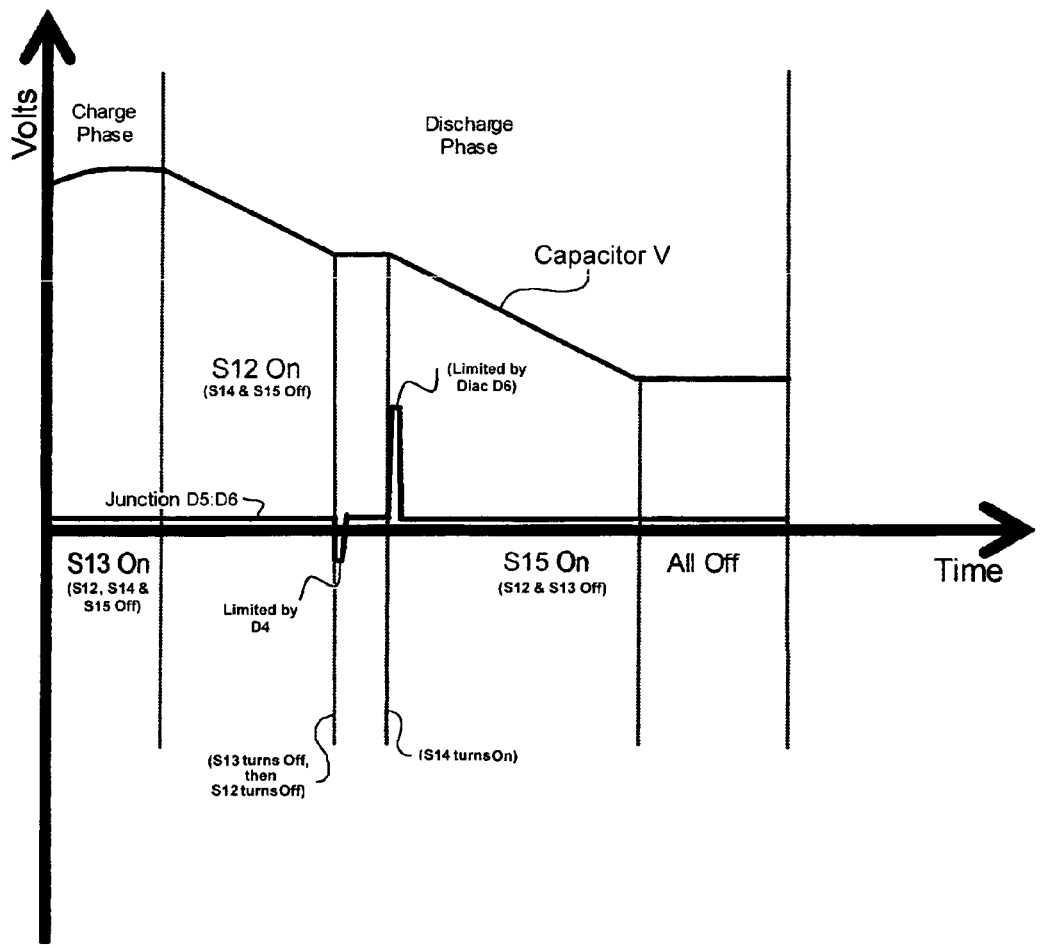
FIG. 5 is a waveform diagram illustrating the internal operation of the H-bridge of FIG. 2.

In the H-bridge 10' according to the embodiment of the invention, FIG. 2, one of the SCRs in the high legs of the H-bridge 10, in the present embodiment the SCR S11, has been replaced by an automatic switching device (ASD) S15. The internal components of the ASD S15 are shown in FIG. 3, where D1 is a capacitor, D2, D3, D5 and D7 are resistors, D4 is a diode, D6 is a diac and D8 is an SCR. The operation of the modified H-bridge 10' will now be described with additional reference to FIGS. 4 and 5 (in the following description it is assumed that the resistances of D2 and D5 are sufficiently small that the voltage on the LHS of the diac D6 is substantially the same as the voltage at the junction of D1 and D3, and that the resistance of D7 is sufficiently small that the voltage on the RHS of the diac D6 is substantially the same as the voltage at the junction of S15 and S13).

The first part of the bipolar delivery into the load (i.e. the patient) is initiated by switching on the IGBT S13. This is achieved by applying and maintaining an external trigger signal to Control 3 to its gate. The capacitor V is then charged, using an external charging circuit, from zero to its required voltage for delivery into the load at the required current. As before, it is necessary that the capacitor V is not pre-charged prior to S13 being switched on since any voltage appearing instantaneously across an SCR (such as the SCR D8 in the ASD S15) may spontaneously trigger the SCR due to the rate of increase in voltage across it. While S13 is held on and the voltage on the capacitor V is rising, the capacitor D1 also charges to the same voltage as capacitor V via S13 and the series resistor D3. The input to the diac D6 is held below its trigger threshold by the low series resistance of S13 and D3, thereby ensuring that the SCR D8 remains switched off.

When the required voltage is reached on the capacitor V, the first portion of current is passed through the load by switching on the SCR S12 by applying a transformer-coupled pulse Control 2 to its gate. With S12 and S13 both switched on, current is passed through the load. The first part of the bipolar delivery into the load is completed by switching off the IGBT S13 by the removal of the external gate signal Control 3. The IGBT S13 switches off almost instantaneously, much faster than the SCR S12 can react to the interruption of current flow, such that the voltage at the junction of S13 and S15 rises to that remaining on the capacitor V by conduction via the load, which is typically 50 ohms. The voltage at the junction of D1 and D3 also rises towards that remaining on capacitor V, but cannot do so instantaneously because of the time constant associated with capacitor D1. This voltage thus lags behind that at the junction of S13 and S15 and would produce a large negative spike across D3 were it not for diode D4. The net result is that the voltage across capacitor D1 is now substantially zero, with both terminals being at a potential approximately equal to that remaining on capacitor V. Some time after IGBT S13 switches off, the SCR S12 switches off, and no further current passes through the load.

The second part of the bipolar delivery into the load is initiated by switching on the IGBT S14 by applying and maintaining an external trigger signal Control 4 to its gate. When switching on, S14 causes the voltage at the junction of S15 and S13 to fall rapidly. The voltage at the junction of D1 and D3 also begins to fall but because of the aforementioned time constant action it cannot do so instantaneously. The lagging voltage this time produces a positive spike across D3, which exceeds the threshold voltage of the diac D6 and switches on the SCR D8. With S14 and S15 both switched on, current passes through the load in the opposite direction to that during the first part of the bipolar discharge. The cycle ends when either the IGBT S14 is switched off by removal of the external signal Control 4 from its gate or by the gradual discharge of the primary voltage source of the capacitor V to a point at which the SCR D8 can no longer support the reduced current flow in the load.

In summary, the control circuitry D1-D7 associated with the SCR D8 in the ASD S15 automatically switches the SCR D8 on, without the need for any external control signal, in response to the change in voltage across the anode and cathode of the SCR D8 when S14 switches on. The ASD removes the limitations of the USD (U.S. Pat. No. 6,996,436) by permitting the switching of much lower AED voltages, yet retains the minimum of components need to implement, and ensure the integrity of, the bridge.

The invention is not limited to the embodiment described herein which may be modified or varied without departing from the scope of the invention.

The invention claimed is:

1. An external defibrillator comprising an H-bridge for delivering bipolar electrotherapy to a patient, the H-bridge having:
   (a) a respective solid state switching device in each of its four legs, the switching device in at least one of the high legs of the H-bridge including an SCR,
   (b) an input for applying an external control signal to the switching device in the low leg diagonally opposite said at least one high leg, wherein turning on the switching device in said diagonally opposite low leg causes a voltage increase across the SCR in said at least one high leg, and
   (c) a control circuit in said at least one high leg, the control circuit comprising a capacitor connected in parallel with the anode-gate path of the SCR, the capacitor having a time constant which generates a voltage spike at the gate of the SCR in response to said voltage increase across the SCR, said spike turning on the SCR,
   whereby the SCR is turned on without the application of an external control signal to said high leg control circuit.

2. The defibrillator of claim 1, wherein the voltage spike is applied to the gate of the SCR via a voltage threshold device connected in series between the capacitor and the gate.

3. The defibrillator of claim 2, wherein the voltage threshold device comprises a diac.

4. The defibrillator of claim 2, wherein the control circuit further comprises a diode connected between the capacitor and the gate in parallel with the voltage threshold device.

* * * * *